(12) United States Patent
Einen et al.

(10) Patent No.: US 10,711,319 B2
(45) Date of Patent: Jul. 14, 2020

(54) METHOD FOR TREATING CELLULOSIC MATERIAL

(71) Applicant: SilvaNova, LLC, Plymouth, MN (US)

(72) Inventors: Jorn Einen, Blomsterdalen (NO); Line Amundsen, Bergen (NO); Andrew Dustan, Os (NO); Aharon Eyal, Jerusalem (IL)

(73) Assignee: SilvaNova, LLC, Plymouth, MN (US)

( * ) Notice: Subject to any disclaimer, the term of this patent is extended or adjusted under 35 U.S.C. 154(b) by 571 days.

(21) Appl. No.: 15/104,466

(22) PCT Filed: Dec. 18, 2014

(86) PCT No.: PCT/GB2014/053752
§ 371 (c)(1),
(2) Date: Sep. 21, 2017

(87) PCT Pub. No.: WO2015/097445
PCT Pub. Date: Jul. 2, 2015

(65) Prior Publication Data
US 2019/0032159 A1    Jan. 31, 2019

(30) Foreign Application Priority Data

Dec. 24, 2013 (GB) .................................. 1322980.2
May 6, 2014 (GB) .................................. 1407970.1

(51) Int. Cl.
| *C13K 1/04* | (2006.01) |
| *C13K 1/02* | (2006.01) |
| *C07H 1/08* | (2006.01) |
| *B01D 11/04* | (2006.01) |

(52) U.S. Cl.
CPC ............ *C13K 1/04* (2013.01); *B01D 11/0492* (2013.01); *C07H 1/08* (2013.01); *C13K 1/02* (2013.01); *C12P 2203/00* (2013.01); *Y02E 50/16* (2013.01)

(58) Field of Classification Search
None
See application file for complete search history.

(56) References Cited

U.S. PATENT DOCUMENTS

| 4,608,245 A * | 8/1986 | Gaddy ...................... C13K 1/04 127/37 |
| 8,052,953 B2 * | 11/2011 | Chen ....................... C01B 17/90 127/37 |
| 2012/0135489 A1 * | 5/2012 | Weydahl .................. C07H 1/08 435/165 |

* cited by examiner

*Primary Examiner* — Stefanie J Cohen
(74) *Attorney, Agent, or Firm* — O'Connor & Company; Ryan P. O'Connor

(57) ABSTRACT

The present invention provides a method comprising: (i) contacting a cellulose-comprising input material with an aqueous hydrolyzing solution comprising at least 35% wt. of at least one mineral acid to form a hydrolyzate comprising a mixture of water-soluble carbohydrates and optionally a solid fraction; (ii) contacting said hydrolyzate with an extractant comprising a first solvent S1, to form a first (preferably solid) residue (preferably comprising precipitated carbohydrates, e.g. mono-, di- and/or oligo-saccharides) and an acid-comprising extract; (iii) separating said acid-comprising extract from said first residue; (iv) modifying said acid-comprising extract to form a second (preferably liquid) residue (preferably comprising dissolved carbohydrates) and an acid-comprising modified extract; (v) fractionating said modified extract into an S1-enriched fraction and an acid-enriched fraction; (vi) reusing said Sl-enriched fraction to form said extractant; and (vii) reusing said acid-enriched fraction to form said aqueous hydrolyzing solution; wherein (a) at least 10% wt. of the cellulose is hydrolyzed and said mixture of water-soluble carbohydrates comprises monosaccharides, disaccharides and/or oligosaccharides; (b) S1 forms a single phase when mixed with an identical weight of 70% sulfuric acid aqueous solution at 25° C.; (c) S1 comprises at least 65% wt. of said extractant; and (d) said acid-comprising extract comprises at least 60% wt. of the acid and at least 5% wt. of the carbohydrates in said hydrolyzate.

19 Claims, No Drawings

METHOD FOR TREATING CELLULOSIC MATERIAL

The invention is in the field of processing cellulose-comprising input material by means of strong mineral acids, e.g. phosphoric and/or sulfuric acid, to produce water soluble carbohydrates. More specifically, the invention deals with separating said mineral acid from formed hydrolyzate by means of organic solvents to achieve high yield of acid recovery and high yield of soluble carbohydrates production.

Large scale conversion of cellulose and lignocellulose materials into sugars (carbohydrates) and lignin products could be useful for supplementing natural gas or crude oil for the production of fuels and platform chemicals. Cellulose and lignocellulose are generally non-food resources and are considered sustainable resources by many production methods. Sources of cellulose and lignocellulose that may be industrially applicable feedstocks include: wood, forest and agricultural residues and wastes, waste-paper, cotton or cotton waste, municipal waste, papermaking wastes, biomass sludges etc. Typically these feedstocks will contain, cellulose, hemicellulose, glucans, lignin, minerals, salts and a range of organic compounds or so-called 'extractives'.

Some form of pretreatment process is generally required to separate lignin from cellulose and/or to convert the cellulose and hemicellulose into carbohydrates that can be processed further. These carbohydrates include C5 (pentose) and C6 (hexose) sugars. Pretreatment methods include the use of strong and weak acids, enzymes, thermomechanical processing, supercritical fluids and organic and inorganic solvents.

Inorganic acids, such as $H_3PO_4$ and $H_2SO_4$, as a result of their high proton activity, can catalyse both decrystallisation of cellulose and the hydrolysis of hemicellulose and cellulose to mono-, di- and oligosaccharides. The acid is itself not consumed by these processes. A certain amount of acid may, however, be consumed by reversible or irreversible reactions such as neutralisation of basic components and esterification.

An economic prerequisite for industrial use of concentrated acids such as $H_3PO_4$ and $H_2SO_4$ is that these can be recovered and reused to a large degree. There are several methods for recovering acid from a cellulose or lignocellulose hydrolysate, including chromatographic separation, membrane separation and solvent extraction.

Organic solvents with suitable solvent characteristics can be used to extract acid from a hydrolysate. The ideal solvent is one which effectively dissolves acid, but not sugar nor lignin and preferably not water. It is also necessary that after acid extraction the solvent and acid can be economically separated for reuse. Such separation can be by evaporation of the solvent from the acid. Alternatively the first solvent could be extracted by a second solvent having suitable properties. An important issue in the solvent selection is also the chemical stability in the presence of acid, particularly if these are heated. Strong acids have a tendency to catalyse condensation, dehydration or esterification reactions in many organic solvents.

The selection of acid, solvents and processing conditions depends on a number of criteria. The combination of variables selected affects the process economics, product yields, wastes generated, and nature of the sugar and lignin products. Downstream processing of sugars may be by catalytic processes, bacterial fermentation or yeast fermentation. In the cases of fermentation, the presence of inhibitory impurities affects the economics and usability of the sugar product. Examples of chemical downstream processes for sugar include production of sugar alcohols by hydrogenation such as xylitol form xylose, production of platform chemicals such as furfural, hydroxymethyl furfural and levulininc acid by dehydration of pentose and hexose sugars. Examples of biological downstream processes includes the production of solvents and organic acids by fermentation, production of enzymes for industrial or other usage and biomass production for use as feed or fodder.

In a first aspect the present invention provides a method comprising (i) contacting a cellulose-comprising input material with an aqueous hydrolyzing solution comprising at least 35% wt. of at least one mineral acid to form a hydrolyzate comprising a mixture of water-soluble carbohydrates and optionally a solid fraction; (ii) contacting said hydrolyzate with an extractant comprising a first solvent S1, to form a first residue and an acid-comprising extract; (iii) separating said acid-comprising extract from said first residue; (iv) modifying said acid-comprising extract to form a second residue and an acid-comprising modified extract; (v) fractionating said modified extract into an S1-enriched fraction and an acid-enriched fraction; (vi) reusing said S1-enriched fraction to form said extractant; and (vii) reusing said acid-enriched fraction to form said aqueous hydrolyzing solution; wherein S1 forms a single phase when mixed with an identical weight of 70% sulfuric acid aqueous solution at 25° C. Preferably, S1 comprises at least 65% wt. of said extractant. Preferably, at least 10% wt. of the cellulose is hydrolyzed and said mixture of water-soluble carbohydrates comprises monosaccharides, disaccharides and/or oligosaccharides and/or said acid-comprising extract comprises at least 60% wt. of the acid and at least 5% wt. of the carbohydrates in said hydrolyzate.

In a preferred aspect the present invention provides a method comprising (i) contacting a cellulose-comprising input material with an aqueous hydrolyzing solution comprising at least 35% wt. of at least one mineral acid to form a hydrolyzate comprising a mixture of water-soluble carbohydrates and optionally a solid fraction; (ii) contacting said hydrolyzate with an extractant comprising a first solvent S1, to form a first residue and an acid-comprising extract; (iii) separating said acid-comprising extract from said first residue; (iv) modifying said acid-comprising extract to form a second residue and an acid-comprising modified extract; (v) fractionating said modified extract into an S1-enriched fraction and an acid-enriched fraction; (vi) reusing said S1-enriched fraction to form said extractant; and (vii) reusing said acid-enriched fraction to form said aqueous hydrolyzing solution; wherein (a) at least 10% wt. of the cellulose is hydrolyzed and said mixture of water-soluble carbohydrates comprises monosaccharides, disaccharides and/or oligosaccharides; (b) S1 forms a single phase when mixed with an identical weight of 70% sulfuric acid aqueous solution at 25° C.; (c) S1 comprises at least 65% wt. of said extractant (i.e. at least 65 wt % of the extractant is S1, which may be a single solvent or solvent mixture); and (d) said acid-comprising extract comprises at least 60% wt. of the acid and at least 5% wt. of the carbohydrates in said hydrolyzate.

According to an embodiment, the weight ratio of said mineral acid in said aqueous hydrolyzing solution to cellulose in said input material is greater than 0.5. According to an embodiment, said weight ratio is less than 20. According to another embodiment, said aqueous hydrolyzing solution comprises a mixture of sulfuric acid and phosphoric acid. According to another embodiment, said contacting with an aqueous hydrolyzing solution is conducted, at least partially, at a temperature in a range between 15 and 80. According to still another embodiment, monosaccharides form less than 85% wt. of the carbohydrates in said hydrolyzate.

According to an embodiment, said S1 is, or comprises, a solvent selected from the group consisting of alcohols comprising 3 to 6 carbon atoms and mixtures thereof. According to another embodiment, said S1 is, or comprises, a solvent selected from the group consisting of tert-butyl alcohol (TBA) tert-amyl alcohol (TAA) and mixtures thereof. S1 can be a mixture of solvents, that is, the term "first solvent S1" as used herein is intended to encompass the situation where S1 can be a mixture of two or more solvents. A similar interpretation of "second solvent S2" is intended. Thus, for example, the requirement that "S1 comprises at least 65% wt of said extractant" means that at least 65 wt % of the extractant is S1, i.e. a single solvent or mixture of solvents make up at least 65 wt % of the extractant (e.g. 35 wt % TBA and 30 wt % TAA). S1 is, or comprises, a solvent, solvent mixture, or mixture of solvents that form a single phase when mixed with an identical weight of 70% sulfuric acid aqueous solution at 25° C., i.e. the solvents of the extractant are miscible with acid. Thus, the invention is counter-intuitive in that it uses something miscible in acid to separate acid from a mixture. Where S1 is, or comprises, a mixture of solvents, it is typically the S1 solvent mixture as a whole which is required to form a single phase when mixed with an identical weight of 70% sulfuric acid aqueous solution at 25° C.

According to an embodiment, said extractant comprises S2. According to various embodiments, said S2 has solubility in water of less than 6% at 25° C. and/or S2 is, or comprises, a solvent selected from the group consisting of saturated and unsaturated C5 to C12 hydrocarbons, dichloromethane, chloroform, halogen-substituted hydrocarbon and fluorine-substituted hydrocarbons.

According to an embodiment, acid content of said first residue is less than 500 Kg per ton of said input material. According to another embodiment, said acid-comprising extract comprises less than 80% wt. of the carbohydrates in said hydrolyzate.

According to an embodiment, said modifying said acid-comprising extract comprises combining said extract with a second solvent S2, preferably wherein said extractant comprises S2. According to related embodiments, S2/S1 wt./wt. ratio in said modified extract is less than 2 and/or greater than 0.01. According to another related embodiment, S1 is tert-amyl alcohol and S2/S1 wt./wt. ratio in said modified extract is greater than 0.01 and/or is less than 2.

According to an additional or alternative embodiment, said modifying said acid-comprising extract comprises changing the temperature of said extract. According to a related embodiment, said changing the temperature comprises lowering the temperature of said acid-comprising extract by at least 10° C.

According to an additional or alternative embodiment, said modifying said acid-comprising extract comprises evaporating a fraction of S1 in said extract.

According to various embodiments, said second residue comprises at least 30% wt. of the acid-comprising extract carbohydrates and/or less than 50% wt. of the acid-comprising extract acid. According to additional embodiments, acid content of said second residue is less than 200 Kg per ton of said input material and/or water content in said second residue is greater than 70% of the water content of said input material.

According to various embodiments, carbohydrate/acid wt./wt. ratio in said second residue is greater than carbohydrate/acid wt./wt. ratio in said acid-comprising extract by a factor of at least 2 and/or greater than soluble carbohydrate/acid wt./wt. ratio in said hydrolyzate.

According to an embodiment, said fractionating said acid-comprising modified extract comprises contacting with S2. According to a related embodiment, said reusing said S1-enriched fraction comprises separation of S1 from S2 by distillation. According to an embodiment, acid/water wt./wt. ratio in said acid-enriched fraction is greater than 80% of that ratio in said hydrolyzing solution.

According to an embodiment, the method comprises combining at least a fraction of said first residue with at least a fraction of said second residue to form a mixed residue and heating said mixed residue, whereby oligosaccharides hydrolyze.

In said first aspect, the present invention further provides a carbohydrate mixture produced according to said method, comprising at least 1 ppm of S1 selected from the group consisting of tert-butyl alcohol and tert-amyl alcohol.

In a second aspect (which may optionally be combined with the first aspect described above), the present invention provides a method comprising (i) contacting a cellulose-comprising input material with an aqueous hydrolyzing solution comprising at least 35% wt. of at least one mineral acid to form a hydrolyzate comprising a mixture of water-soluble carbohydrates and optionally a solid fraction; (ii) contacting said hydrolyzate with an extractant comprising a first solvent S1 and a second solvent S2 to form a residue and an acid-comprising extract; (iii) separating said acid-comprising extract from said residue; (iv) fractionating said acid-comprising extract into an S1-enriched fraction and an acid-enriched fraction; (v) reusing said S1-enriched fraction to form said extractant; and (vi) reusing said acid-enriched fraction to form said aqueous hydrolyzing solution, wherein S1 forms a single phase when mixed with an identical weight of 70% sulfuric acid aqueous solution at 25° C. and S2 has a solubility in water of less than 6% at 25° C. Preferably, S1 comprises at least 65% wt. of said extractant and/or S2 comprises at least 1% wt. of said extractant. Especially preferably, at least 10% wt. of the cellulose is hydrolyzed and said mixture of water-soluble carbohydrates comprises monosaccharides, disaccharides and/or oligosaccharides; and/or said extract comprises at least 70% wt. of the acid and less than 10% wt. of the carbohydrates in said hydrolyzate.

The second aspect preferably provides a method comprising (i) contacting a cellulose-comprising input material with an aqueous hydrolyzing solution comprising at least 35% wt. of at least one mineral acid to form a hydrolyzate comprising a mixture of water-soluble carbohydrates and optionally a solid fraction; (ii) contacting said hydrolyzate with an extractant comprising a first solvent S1 and a second solvent S2 to faun a residue and an acid-comprising extract; (iii) separating said acid-comprising extract from said residue; (iv) fractionating said acid-comprising extract into an S1-enriched fraction and an acid-enriched fraction; (v) reusing said S1-enriched fraction to form said extractant; and (vi) reusing said acid-enriched fraction to form said aqueous hydrolyzing solution, wherein (a) at least 10% wt. of the cellulose is hydrolyzed and said mixture of water-soluble carbohydrates comprises monosaccharides, disaccharides and/or oligosaccharides; (b) S1 forms a single phase when mixed with an identical weight of 70% sulfuric acid aqueous solution at 25° C. and comprises at least 65% wt. of said extractant; (c) S2 has a solubility in water of less than 6% at 25° C. and comprises at least 1% wt. of said extractant; and (d) said extract comprises at least 70% wt. of the acid and less than 10% wt. of the carbohydrates in said hydrolyzate.

According to an embodiment, the weight ratio of said mineral acid in said aqueous hydrolyzing solution to cellulose in said input material is greater than 0.5. According to an embodiment, said weight ratio is less than 20. According to another embodiment, said aqueous hydrolyzing solution comprises a mixture of sulfuric acid and phosphoric acid. According to another embodiment said contacting with an aqueous hydrolyzing solution is conducted, at least partially, at a temperature in a range between 15 and 80. According to still another embodiment, monosaccharides form less than 85% wt. of the water-soluble carbohydrates in said hydrolyzate.

According to an embodiment, said S1 is, or comprises, a solvent selected from the group consisting of alcohols comprising 3 to 6 carbon atoms and mixtures thereof.

According to another embodiment, said S1 is, or comprises, a solvent selected from the group consisting of tert-butyl alcohol, tert-amyl alcohol and mixtures thereof.

According to an embodiment, S2 is, or comprises, a solvent selected from the group consisting of saturated and unsaturated C5 to C12 hydrocarbons, dichloromethane, chloroform, halogen-substituted hydrocarbon and fluorine-substituted hydrocarbons.

According to various embodiment, S2/S1 wt./wt. ratio in said extractant is less than 2 and/or greater than 0.01. According to additional or alternative embodiments, S1 is, or comprises, tert-amyl alcohol and S2/S1 wt./wt. ratio in said extractant is greater than 0.01 and/or is less than 2. According to alternative embodiments, S1 is, or comprises, tert-butyl alcohol and S2/S1 wt./wt. ratio in said extractant is greater than 0.01 and/or is less than 2.

According to an embodiment, acid/carbohydrate wt./wt. ratio in said extract is greater than acid/soluble carbohydrate wt./wt. ratio in said hydrolyzate by a factor of at least 2.

According to an embodiment, acid content of said first residue is less than 500 Kg per ton of said input material. According to an embodiment, the method comprises comprising heating said residue, whereby oligosaccharides hydrolyze.

According to an embodiment, said fractionating said extract comprises contacting with S2. According to a related embodiment, said reusing said S1-enriched fraction comprises separation of S1 from S2 by distillation.

In said second aspect, the present invention also provides a carbohydrate mixture produced according to said method, comprising at least 1 ppm of S1 selected from the group consisting of tert-butyl alcohol and tert-amyl alcohol.

According to a first aspect, the present invention provides a method comprising (i) contacting a cellulose-comprising input material with an aqueous hydrolyzing solution comprising at least 35% wt. of at least one mineral acid to form a hydrolyzate comprising a mixture of water-soluble carbohydrates and optionally a solid fraction; (ii) contacting said hydrolyzate with an extractant comprising a first solvent S1, to form a first (preferably solid) residue (preferably comprising precipitated carbohydrates, e.g. mono-, di- and/or oligo-saccharides) and an acid-comprising extract; (iii) separating said acid-comprising extract from said first residue; (iv) modifying said acid-comprising extract to form a second (preferably liquid) residue (preferably comprising dissolved carbohydrates) and an acid-comprising modified extract; (v) fractionating said modified extract into an S1-enriched fraction and an acid-enriched fraction; (vi) reusing said S1-enriched fraction to form said extractant; and (vii) reusing said acid-enriched fraction to form said aqueous hydrolyzing solution; wherein (a) at least 10% wt. of the cellulose is hydrolyzed and said mixture of water-soluble carbohydrates comprises monosaccharides, disaccharides and/or oligosaccharides; (b) S1 forms a single phase when mixed with an identical weight of 70% sulfuric acid aqueous solution at 25° C.; (c) S1 comprises at least 65% wt. of said extractant; and (d) said acid-comprising extract comprises at least 60% wt. of the acid and at least 5% wt. of the carbohydrates in said hydrolyzate. In further aspects, as noted above, features (a), (c) and (d) are independently optional.

According to an embodiment, said cellulose-comprising input material comprises at least 20% wt., at least 25% wt., at least 30% wt., at least 35% wt. or at least 40% wt. cellulose on a water-free basis. According to another embodiment, the cellulose comprised in said input material has a degree of crystallinity of at least 20%, at least 40% or at least 60%. According to additional or alternative embodiments, said input material further comprises, on same basis, at least 10% wt., at least 15% wt., or at least 20% wt. hemicellulose, and/or at least 15% wt., at least 20% wt., or at least 25% wt. lignin. According to another embodiment, the input material have a content of marine origin polymers containing sugars and/or sugar alcohols and at least 10% wt., at least 25% wt., at least 30% wt., at least 35% wt. or at least 40% wt. cellulose, on a dry basis.

According to another embodiment, said cellulose-comprising input material is selected from a group of lignocellulosic materials consisting of softwood, hardwood, bagasse, agricultural and forestry residues, switchgrass, and other cellulose containing energy crops, waste from refined cellulose products such as textiles, and bio-based insulation, refused construction wood, metal and creosote impregnated wood, and other sugar polymers selected from the group consisting of carrageenan, agar and laminarin, and other cellulose containing waste such as municipal solid waste, and cellulose containing feces, and waste paper and cardboard and refined cellulose or modified cellulose products such as cellulose pulp and dissolving pulps originating from Kraftprocess, sulfiteprocess, organosolve or other pulping process.

Additionally or alternatively, such lignocellulosic materials is treated prior to contacting with said aqueous hydrolyzing solution and said pre-treatment comprises at least one of pre-hydrolyzing at least a fraction of hemicellulose content, adjustment of moisture content, e.g. drying, extraction, e.g. of lignin and/or extractables or extracting limonene from orange peels and comminution. According to an embodiment, said cellulose-comprising input material comprises moisture and said moisture content is between 1% wt. and 40% wt., between 2% wt. and 30% wt., between 3% wt. and 25% wt., or between 4% wt. and 20% wt.

Said cellulose-comprising input material is contacted with an aqueous hydrolyzing solution comprising at least 35% wt. of at least one mineral acid. According to various embodiments, said at least one mineral acid is selected from sulfuric acid, phosphoric acid and mixtures thereof. According to another embodiment, mineral acid content in said hydrolyzing solution is at least 40% wt., at least 50% wt., at least 60% wt., at least 65% wt. or at least 70% wt. According to still another embodiment, mineral acid content in said hydrolyzing solution is less than 90% wt., less than 85% wt., less than 80% wt., less than 75% wt., or less than 70% wt.

According to an embodiment, the weight ratio of said mineral acid in said hydrolyzing solution to cellulose in said input material is greater than 0.3, greater than 0.5, greater than 0.7, greater than 0.8, greater than 0.9 or greater than 1.0. According to another embodiment, the weight ratio of said mineral acid in said hydrolyzing solution to cellulose in said input material is less than 20, less than 15, less than 10, or less than 5.

According to an embodiment, said contacting with an aqueous hydrolyzing solution is conducted, at least partially, at a temperature greater than 15° C., greater than 20° C., greater than 25° C., greater than 30° C., greater than 35° C., or greater than 40° C. According to an embodiment, said contacting with an aqueous hydrolyzing solution is conducted, at least partially, at a temperature lower than 80° C., lower than 70° C., lower than 60° C., lower than 55° C., lower than 50° C., or lower than 40° C. According to another embodiment, said contacting with an aqueous hydrolyzing solution is conducted, at least partially, at a temperature in the range between 10° C. and 80° C., between 20° C. and 70° C., or between 30° C. and 60° C.

Any form of contacting said input material with said aqueous hydrolyzing solution is suitable, e.g. mixing.

Said contacting with an aqueous hydrolyzing solution results in cellulose hydrolysis. As used herein, hydrolysis means reducing the molecular weight of cellulose. Said hydrolysis forms a hydrolyzate comprising a mixture of water-soluble carbohydrates and optionally a solid fraction. According to an embodiment, said input material comprises lignin and lignin forms at least a portion of said solid fraction. According to the method of the first aspect, at least 10%, at least 20%, at least 30%, at least 40% or at least 50% of the cellulose is hydrolyzed to form a mixture of water-soluble carbohydrates. As used herein, the degree of hydrolysis is the weight ratio between the total amount of water-soluble carbohydrates and the amount of cellulose in said input material. Said mixture comprises monosaccharides, disaccharides and/or oligosaccharides (preferably all three). As used herein, oligosaccharides are carbohydrates composed of at least 3 monosaccharides. According to an embodiment, said mixture comprises both hexoses and pentoses.

Input materials of the invention differ in characteristics such as cellulose content, composition of other components (e.g. content of hemicellulose and lignin), degree of cellulose crystallinity, moisture content and physical dimensions. These differences lead to differences in the result of said contacting with said aqueous hydrolyzing solution when conducted at identical conditions. These results of contacting include the extent of decrystallization, the degree of hydrolysis and the composition of the carbohydrate mixture.

Contacting parameters can be modified in order to affect the results of contacting. These parameters include acid selection and acid concentration in said hydrolyzing solution, acid to input material weight ratio, contacting temperature and contacting mode. According to an embodiment, those contacting parameters are adjusted to the characteristics of the input material in order to achieve a desired extent of decrystallizing of said cellulose in said input material. As used herein, decrystallizing means reducing the degree of crystallinity, as determined, e.g. by X-ray diffraction microscopy with polarized light, Raman spectroscopy. According to an embodiment, contacting parameters are selected so that the degree of crystallinity is reduced by at least 10%, at least 20%, at least 30%, at least 40%, or at least 50%.

According to an embodiment, those contacting parameters are adjusted to the characteristics of the input material in order to achieve a desired composition of the carbohydrates in said water-soluble carbohydrates mixture. According to an embodiment, monosaccharides form less than 85% wt., less than 75% wt., less than 65% wt., less than 55% wt., or less than 50% wt., of the carbohydrates in said hydrolyzate mixture of water-soluble carbohydrates. According to another embodiment, oligosaccharides form at least 10% wt., at least 20% wt., at least 25% wt., or at least 30% wt., of the carbohydrates in said hydrolyzate mixture of water-soluble carbohydrates.

The method of the first aspect comprises contacting said hydrolyzate with an extractant comprising a first solvent S1, to form a first residue comprising precipitated carbohydrates and an acid-comprising extract. As the first residue is typically solid, this extraction step produces only one liquid phase. S1 is characterized by forming a single phase when mixed with an identical weight of 70% sulfuric acid aqueous solution at 25° C. According to an embodiment, S1 forms a single phase when mixed with 1.5 weights, 2 weights, 2.5 weights, 3.0 weights, 3.5 weight or 4.0 weights of 70% sulfuric acid aqueous solution at 25° C.

According to an embodiment, S1 is, or comprises, a solvent selected from the group consisting of alcohols comprising 3 to 6 carbon atoms and mixtures thereof. According to another embodiment, S1 is, or comprises, a solvent selected from the group consisting of tert-butyl alcohol, tert-amyl alcohol and mixtures thereof. According to an embodiment, S1 is, or comprises tert-amyl alcohol.

According to an embodiment, S1 comprises at least 65% wt., at least 70% wt., at least 75% wt., at least 80% wt., at least 85% wt., or at least 90% wt., of said extractant. According to an embodiment, S1 is the sole organic solvent in said extractant. Additionally or alternatively, said extractant comprises, according to an embodiment, water, e.g. at least 1%, at least 3% or at least 5% water. According to an embodiment, said extractant comprises another organic solvent, (e.g. a water-immiscible ketone such as diethyl ketone), e.g. at least 1%, at least 3% or at least 5% of another solvent.

According to an embodiment, said extractant comprises a second solvent S2. According to an embodiment, S2 has a solubility in water at 25° C. of less than 6% wt., less than 4% wt., less than 3% wt., less than 2% wt., or less than 1% wt. According to another embodiment, S2 is, or comprises, a solvent selected from the group consisting of saturated and unsaturated C5 to C12 hydrocarbons, dichloromethane, chloroform, halogen-substituted hydrocarbon and fluorine-substituted hydrocarbons. According to an embodiment, S2 is, or comprises, a solvent selected from a group consisting of decane and dodecane.

According to various embodiments, said contacting said hydrolyzate with an extractant is of multiple steps and is conducted in a counter-current or a cross-current mode. According to another embodiment, in said contacting, extractant to hydrolyzate flux wt./wt. ratio is in a range between 1:1 and 10:1, between 1.1:1 and 8:1, between 1.2:1 and 6:1 or between 1.3:1 and 4:1. According to an embodiment, said contacting is conducted at a temperature in the range between 1° C. and 60° C., between 5° C. and 55° C., or between 10° C. and 50° C.

Said contacting said hydrolyzate with an extractant forms a first residue (e.g. a solid phase comprising precipitated carbohydrates) and an acid-comprising extract. The first residue is typically a solid (or at least denser) phase, e.g. materials precipitate during extraction. Step (ii) of all embodiments of the invention therefore involves precipitation of carbohydrates. This enables carbohydrates and lignin to be separated from the majority of the acid and gives only one liquid phase, which is easier to handle than two liquid phases. Said first residue typically comprises one or more of mineral acid, water-soluble carbohydrates (e.g. monosaccharides, disaccharides and/or oligosaccharides), optionally cellulose and optionally a solid fraction (e.g. comprising lignin). The extractant and/or solvents therein (e.g. S1) are preferably capable of precipitating carbohydrates. Since the majority of the acid in the hydrolyzate transfers to the extractant, the first residue is depleted in acid. According to another embodiment, the mineral acid content of said first residue is less than 500 Kg, less than 400 Kg, less than 300 Kg, less than 200 Kg, or less than 100 Kg, per ton of said input material. As used herein, the term acid-comprising extract means a phase preferably comprising at least 70% of the total amount of S1, at least a fraction of said mineral acid and water-soluble carbohydrate. Said acid-comprising extract preferably comprises at least 60% wt., at least 70% wt., at least 80% wt., at least 90% wt., at least 92% wt. or at least 94% wt. of the mineral acid in said hydrolyzate. Said acid-comprising extract further preferably comprises at least 5% wt., at least 10% wt., at least 15% wt., or at least 20% wt. of the carbohydrates in said hydrolyzate, i.e. preferably some carbohydrates enter the extract. This embodiment of the invention therefore prioritizes acid extraction over sugar (carbohydrate) extraction. According to an embodiment, said extract preferably comprises less than 80% wt., less than 70% wt., less than 60% wt., less than 50% wt., less than 40% wt., less than 30% wt., or less than 20% wt., of the carbohydrates in said hydrolyzate.

The method of the first aspect further comprises separating said acid-comprising extract from said first residue and modifying said acid-comprising extract to form a second residue and an acid-comprising modified extract. According to an embodiment, said acid-comprising extract comprises a single liquid phase and said modifying generates two liquid phases: a second residue (typically a heavy/dense, water-rich polar phase), which is heavier and an acid-comprising modified extract, which is lighter. The modification step therefore acts to reject water and carbohydrates (and typically some acid) from the acid-comprising extract. The second residue comprises S2 in addition to water and carbohydrates (and typically some acid) and the remaining modified acid-extract typically comprises the majority of the acid and S1.

According to an embodiment, modifying said separated extract comprises combining said extract with said second solvent S2. Any method of combining is suitable, including simple mixing. Combining said separated extract with S2 generates a heavy phase second residue and a light phase modified extract. Said second residue comprises carbohydrates, optionally said mineral acid, optionally S1 and optionally S2. Said modified extract comprises optionally S1, optionally S2, said mineral acid and optionally carbohydrates. According to an embodiment, said modified extract comprises at least 70% wt., at least 80% wt., at least 85% wt., at least 90% wt., or at least 95% wt. of the S1. According to an embodiment, said modified extract comprises at least 90% wt., at least 92% wt., at least 94% wt., at least 96% wt., at least 98% wt. or at least 99% wt. of the S2.

According to an embodiment, S2/S1 wt./wt. ratio in said modified extract is less than 2, less than 1.5, less than 1, less than 0.8, less than 0.6, less than 0.4, or less than 0.2. According to another embodiment, S2/S1 wt./wt. ratio in said modified extract is greater than 0.01, greater than 0.05, greater than 0.1, greater than 0.15, or greater than 0.2.

According to an embodiment, S2 is a hydrocarbon, S1 is tert-amyl alcohol and preferably S2/S1 wt./wt. ratio in said modified extract is less than 2, less than 1.5, less than 1, less than 0.8, less than 0.6, less than 0.4, or less than 0.2. According to another embodiment, S2 is a hydrocarbon, S1 is tert-amyl alcohol and S2/S1 wt./wt. ratio in said modified extract is greater than 0.01, greater than 0.05, greater than 0.1, greater than 0.15, or greater than 0.2.

According to an additional or an alternative embodiment, modifying said separated extract comprises evaporating a fraction of S1 in said extract. As used herein, the terms evaporation and distillation are used interchangeably. According to an embodiment, at least 1% wt., at least 2% wt., at least 4% wt., at least 6% wt., at least 8% wt., or at least 10% wt., of S1 in the extract is evaporated. According to an embodiment, less than 25% wt., less than 20% wt., less than 18% wt., less than 16% wt., less than 14% wt., less than 12% wt., or less than 10% wt., of S1 in the extract is evaporated. Said evaporating a fraction of S1 generates a heavy phase second residue and a light phase modified extract. Said second residue comprises carbohydrates, optionally said mineral acid and optionally S1. Said modified extract comprises S1, said mineral acid and optionally carbohydrates.

According to an additional or an alternative embodiment, modifying said separated extract comprises changing the temperature of said extract. According to an embodiment changing the temperature of said extract comprises heating said extract. According to an embodiment changing the temperature of said extract comprises cooling said extract. According to an embodiment the temperature of said extract is changed by at least 5° C., at least 10° C., at least 15° C., at least 20° C., or at least 25° C. According to an embodiment the temperature of said extract is changed by less than 60° C., less than 50° C., less than 40° C., or less than 30° C. Said changing the temperature of said extract generates a heavy phase second residue and a light phase modified extract. Said second residue comprises carbohydrates, optionally said mineral acid and optionally S1. Said modified extract comprises S1, said mineral acid and optionally carbohydrates.

According to an embodiment, modifying said separated extract comprises at least one of combining said extract with said second solvent S2, evaporating a fraction of S1 in said extract, changing the temperature of said extract and combinations thereof.

According to an embodiment, at least a fraction of said second residue is combined with said hydrolyzate prior to contacting with said extractant. According to an additional or an alternative embodiment, at least a fraction of said second residue, is heated, whereby oligosaccharides hydrolyze, to form an aqueous solution comprising low molecular weight carbohydrates and mineral acid.

According to an embodiment, said modified extract comprises at least 60% wt., at least 70% wt., at least 80% wt., or at least 90% wt., of the acid in the extract, i.e. the vast majority of the acid originally present in the extract stays after modification in the modified extract. According to an embodiment, said modified extract comprises less than 60% wt., less than 50% wt., less than 40% wt., less than 30% wt., less than 20% wt., or less than 10% wt., of the carbohydrates in the extract, i.e. the vast majority of the carbohydrates originally present in the extract end up in the second residue.

According to an embodiment, said second residue comprises less than 50% wt., less than 40% wt., less than 30% wt., less than 20% wt., or less than 10% wt., of the acid in the extract, i.e. the vast majority of the acid originally present in the extract stays in the modified extract. According to an embodiment, acid content of said second residue is less than 200 Kg, less than 150 Kg, less than 100 Kg, or less than 70 Kg per ton of said input material. According to an embodiment, said second residue comprises at least 30% wt., at least 40% wt., at least 50% wt., at least 60% wt., at least 70% wt., at least 80% wt., or at least 90% wt., of the carbohydrates in the extract, i.e. the vast majority of the carbohydrates originally present in the extract end up in the second residue.

According to these and other embodiments, the majority of the acid originally present in the extract stays in the modified extract, while the majority of the carbohydrates originally present there end up in the second residue, so that carbohydrate/acid wt./wt. ratio in said second residue is greater than carbohydrate/acid wt./wt. ratio in said extract preferably by a factor of at least 2, at least 3, at least 4, at least 5, at least 6, or at least 8. According to another embodiment, carbohydrate/acid wt./wt. ratio in said second residue is greater than carbohydrate/acid wt./wt. ratio in said hydrolyzate.

Because the extractant is such a good solvent for the hydrolyzing acid (e.g. S1 is a good solvent for the acid), the majority of the solvent remains in the modified extract. As the carbohydrates have a higher affinity for the water phase than the acid does, most of the water and sugars can be rejected in the modification step and enter the second residue (a water-rich polar phase). In contrast to the first residue, the second residue it typically a liquid phase, i.e. a dense liquid carbohydrate phase. The first residue is therefore preferably a solid. The second residue is therefore preferably a liquid.

According to an embodiment, an objective of the method of the first aspect is to convert a large fraction of the cellulose in said cellulose-comprising input material into a product comprising soluble carbohydrates. According to an embodiment, those product soluble carbohydrates are of low molecular weight, preferably monomers. The method comprises contacting said cellulose-comprising input material with a concentrated aqueous hydrolyzing solution comprising at least one mineral acid to form a hydrolyzate. Said contacting with hydrolyzing solution is also referred to herein as decrystallization since, according to an embodiment, it results in decrystallizing cellulose in said input material. Said hydrolyzate comprises a mixture of water-soluble carbohydrates, optionally cellulose and essentially all the mineral acid. The method further comprises a step of separating mineral acid from said hydrolyzate to form a first residue. According to an embodiment, said first residue is, in fact, an acid-depleted hydrolyzate. According to an embodiment, at least a fraction of said first residue, is heated, whereby oligosaccharides hydrolyze, along with cellulose, if present, to form an aqueous solution comprising low molecular weight carbohydrates and mineral acid. According to another embodiment, at least a fraction of said first residue is combined with at least a fraction of said second residue and optionally, another stream comprising oligosaccharides and/or cellulose, to form a mixed residue and said mixed residue is heated, whereby oligosaccharides hydrolyze, along with cellulose, if present, to form an aqueous solution comprising low molecular weight carbohydrates and mineral acid. Said oligosaccharides hydrolysis is also referred to herein as second hydrolysis and the aqueous solution formed by said second hydrolysis is also referred to as second hydrolyzate.

According to an embodiment, while said decrystallization is conducted at (catalyzed by) high concentration of mineral acid, said second hydrolysis is conducted at (catalyzed by) low concentration of mineral acid, e.g. less than 8% wt., less than 6% wt., less than 4% wt., or less than 2% wt., when calculated on the basis of acid/(acid+water). According to an embodiment, said second hydrolyzate is contacted with a base, whereby mineral acid comprised therein is neutralized. According to an embodiment, said mineral acid is sulfuric acid, said base is a calcium base, e.g. lime or calcium carbonate, and said neutralizing generates gypsum, which is separated, e.g. by filtration to leave acid-depleted second hydrolyzate. According to an embodiment, said mineral acid is sulfuric and/or phosphoric acid, said base is a sodium base, e.g. sodium hydroxide or sodium carbonate, and said neutralizing generates water soluble sodium sulfate and/or phosphates, which could be separated, e.g. by nanofiltration or dialysis to leave acid depleted second hydrolysate, and a salt solution that could be thrown away or used as nutrient supplementation, or alternatively used without separation as sugar/nutrient salt stream for downstream processes e.g. ethanol fermentation. According to an embodiment, said acid-depleted second hydrolyzate is further treated to form said product, e.g. by at least one of concentrating and polishing.

According to these embodiments, an objective of the method of said first aspect is to separate mineral acid from the hydrolyzate at high yield, leaving in the first residue only the amount of acid required for said second hydrolysis. That is since low yields of mineral acid separation results in major costs related to losses/consumption of said mineral acid, costs of consuming said neutralizing base and costs related to separation and disposal of the generated salt. According to the method, acid is separated from the hydrolyzate by contacting with an extractant comprising a first solvent S1, which forms at least 65% wt. of said extractant and optionally up to 100% of the solvent content therein. Past methods used extractants with an intermediate degree of hydrophilicity, e.g. dialkyl ketones, which led to less than optimal acid separation yield. Possibly, extractants of higher hydrophilicity, e.g. ones having high mutual miscibility with mineral acid solutions, was avoided in past methods since the acid-comprising extract they form contains water-soluble carbohydrates, in addition to the mineral acid. Carbohydrates in the acid-comprising extract are also referred to as co-extracted carbohydrates.

Acid separated from the hydrolyzate by contacting with the extractant ends up in the acid-comprising extract. An economically attractive method for the production of carbohydrates requires recovery (separation) of the acid from the extract for reuse in decrystallization. According to past methods, the acid is recovered as an aqueous solution that is more dilute than the hydrolyzing solution used to form the hydrolyzate. That is due to moisture introduced from other sources, particularly moisture introduced by the input material. Typically, the majority of that moisture or all of it ends up in the extract and then in the recovered acid. Hence, for reuse, according to past methods, said recovered acid needs to be reconcentrated before reused in decrystallization. Since high mineral acid concentrations need to be reached in an economic method, elevated temperatures are not avoidable.

According to past methods, co-extracted carbohydrates end up in the recovered acid. Due to the high concentration of the acid and the elevated reconcentration temperatures, a large fraction of the carbohydrates in the recovered acid is degraded. Said degradation presents product loss and generates degradation products that are difficult to remove and contaminate the carbohydrates formed in the second hydrolysis. According to an embodiment, the formed carbohydrates are used as fermentation feedstock. Some of the degradation products are inhibitory to the fermenting organisms.

Using the above logic, the potential gain in mineral acid separation yield achieved by using more hydrophilic extractants is outweighed by the costs related to reduced carbohydrate yields and generation of related degradation products. This has probably demotivated the use of more hydrophilic extractants, which seems to be the reason for selecting only extractants with an intermediate hydrophilicity.

The method of this first aspect solves these issues and enables combining these seemingly conflicting goals of reaching high acid recovery yield and high carbohydrates production yield. High yield of acid separation from the hydrolyzate is achieved, possibly due to the use of a hydrophilic extractant comprising a solvent S1 having high mutual miscibility with concentrated mineral acid solutions. Carbohydrates are co-extracted with the acid and are found in the acid-comprising extract. Modifying said extract according to the method of this first aspect forms a second residue. The inventors have found that said second residue comprises the majority of the co-extracted carbohydrates, i.e. modifying said extract "rejects" the majority of the co-extracted carbohydrates into said second residue. It was further found that carbohydrates/oligosaccharides of higher molecular weight are better rejected to the second residue, which increases the motivation for adjusting the parameters of decrystallization to the formation of a greater fraction of oligomers in the total amount of water-soluble carbohydrates.

At the same time, said second residue of the first aspect comprises only a small fraction of the acid in said extract. Differently put, the acid-comprising modified extract comprises the majority of the acid to be recycled, but only a minimal fraction of the co-extracted carbohydrate. Hence, acid recovered from said modified extract for reuse in decrystallization has only a minimal fraction of the co-extracted carbohydrate. If required, reconcentrating said acid recovered from this modified extractant does not involve significant carbohydrates degradation, avoiding undesired carbohydrate yield loss.

Furthermore, according to an embodiment, such reconcentration of the acid recovered from the modified extract is not required or is minimal. According to an embodiment, additionally to carbohydrates, water is rejected to said second residue. According to a related embodiment, water content in said second residue is greater than 70% wt., greater than 80% wt., greater than 90% wt., greater than 100% wt., or greater than 110% wt., of the water content of said input material. According to these embodiments, the majority of the water introduced into the hydrolyzate by the input material, or all of it, is removed from the extract into said second residue. As a result, acid recovered from said modified extract is of a concentration similar to that in said hydrolyzing solution, which minimizes or eliminates the need for reconcentrating the acid recovered from the extract.

Hence, the method of the first aspect combines high yield of mineral acid separation from the hydrolyzate, high yields of carbohydrates production and major savings on costs of acid reconcentration.

Typically, the second residue is removed prior to fractionating the modified extract. The modification step therefore purifies the acid-extract of sugars and water.

According to the method of the first aspect, recovering said mineral acid from said modified extract comprises fractionating said modified extract into an S1-enriched (organic) fraction and an acid-enriched (polar) fraction. As used herein, S1-enriched fraction is a fraction having S1/acid wt./wt. ratio greater than that in the modified extract and the acid-enriched fraction is a fraction having acid/S1 wt./wt. ratio greater than that in the modified extract. According to an embodiment, said S1-enriched fraction comprises less than 10% wt., less than 5% wt., less than 4% wt., less than 3% wt., less than 2% wt., or less than 1% wt. acid. According to an embodiment, said acid-enriched fraction comprises less than 10% wt., less than 5% wt., less than 4% wt., less than 3% wt., less than 2% wt., or less than 1% wt. S1.

According to an embodiment, said fractionating preferably comprises contacting said acid-comprising modified extract with S2. According to an embodiment, said acid-comprising modified extract is contacted with S2 to form two fractions, a light S1-enriched phase comprising S1 and S2 and a heavy aqueous acid-enriched phase. According to an embodiment, said contacting is conducted in a counter-current mode. Alternatively, or additionally, said fractionating said acid-comprising modified extract comprises evaporating S1.

The method of the first aspect preferably comprises reusing said S1-enriched fraction to form said extractant. According to an embodiment, said reusing comprises at least one of drying, separation of a bleed for purification and addition of another solvent, e.g. S2. According to another embodiment, wherein said fractionating comprises contacting with S2, said S1-enriched fraction comprises S2 and said reusing said S1-enriched fraction comprises separation of S1 from S2 by distillation.

The method of the first aspect further comprises reusing said acid-enriched fraction to form said aqueous hydrolyzing solution. According to an embodiment, acid/water wt./wt. ratio in said acid-enriched fraction is greater than 80%, greater than 85%, greater than 90%, greater than 95%, or greater than 100%, of that ratio in said hydrolyzing solution. Preferably, the acid-enriched fraction is concentrated prior to reuse. According to an embodiment, said reusing comprises combining with a make-up acid to cover for the acid present in the first residue, in the second residue or both.

The first aspect of the present invention provides a carbohydrate mixture produced according to said method, comprising at least 1 ppm, at least 5 ppm, at least 10 ppm, at least 15 ppm, or at least 20 ppm, of S1. According to a related embodiment, said S1 is, or comprises, a solvent selected from the group consisting of tert-butyl alcohol and tert-amyl alcohol.

According to a second aspect, the present invention provides a method comprising (i) contacting a cellulose-comprising input material with an aqueous hydrolyzing solution comprising at least 35% wt of at least one mineral acid to form a hydrolyzate comprising a mixture of water-soluble carbohydrates and optionally a solid fraction; (ii) contacting said hydrolyzate with an extractant comprising a first solvent S1 and a second solvent S2 to form a (preferably solid) residue (preferably comprising precipitated carbohydrates, e.g. mono-, di- and/or oligo-saccharides) and an acid-comprising extract; (iii) separating said acid-comprising extract from said residue; (iv) fractionating said acid-comprising extract into an S1-enriched fraction and an acid-enriched fraction; (v) reusing said S1-enriched fraction to form said extractant; and (vi) reusing said acid-enriched fraction to form said aqueous hydrolyzing solution; wherein (a) at least 10% wt. of the cellulose is hydrolyzed and said mixture of water-soluble carbohydrates comprises monosaccharides, disaccharides and/or oligosaccharides; (b) S1 forms a single phase when mixed with an identical weight of 70% sulfuric acid aqueous solution at 25° C. and preferably comprises at least 65% wt. of said extractant; (c) S2 has a solubility in water of less than 6% at 25° C. and preferably comprises at least 1% wt. of said extractant; and (d) said extract comprises at least 70% wt. of the acid and less than 10% wt. of the carbohydrates in said hydrolyzate. In further aspects, as noted above, features (a) and (d) are optional.

According to an embodiment, said cellulose-comprising input material comprises at least 20% wt., at least 25% wt., at least 30% wt., at least 35% wt. or at least 40% wt. cellulose on a water-free basis. According to another embodiment, the cellulose comprised in said input material has a degree of crystallinity of at least 20%, at least 40% or at least 60%. According to additional or alternative embodiments, said input material further comprises, on same basis, at least 10% wt., at least 15% wt., or at least 20% wt. hemicellulose, and/or at least 15% wt., at least 20% wt., or at least 25% wt. lignin. According to another embodiment, the input material have a content of marine origin polymers containing sugars and/or sugar alcohols, or at least 10% wt., at least 25% wt., at least 30% wt., at least 35% wt. or at least 40% wt. cellulose, on a dry basis.

According to another embodiment, said cellulose-comprising input material is selected from a group of lignocellulosic materials consisting of softwood, hardwood, bagasse, agricultural and forestry residues, switchgrass, and other cellulose containing energy crops, waste from refined cellulose products such as textiles, and bio-based insulation, refused construction wood, metal and creosote impregnated wood, and other sugar polymers selected from the group consisting of carrageenan, agar and laminarin, and other cellulose containing waste such as municipal solid waste, and cellulose containing feces, and waste paper and cardboard and refined cellulose or modified cellulose products such as cellulose pulp and dissolving pulps originating from Kraftprocess, sulfiteprocess, organosolve or other pulping process.

Additionally or alternatively, such lignocellulosic materials is treated prior to contacting with said aqueous hydrolyzing solution and said pre-treatment comprises at least one of pre-hydrolyzing at least a fraction of hemicellulose content, adjustment of moisture content, e.g. drying, extraction, e.g. of lignin and/or extractables or extracting limonene from orange peels and comminution. According to an embodiment, said cellulose-comprising input material comprises moisture and said moisture content is between 1% wt. and 40% wt., between 2% wt. and 30% wt., between 3% wt. and 25% wt., or between 4% wt. and 20% wt.

Said cellulose-comprising input material is contacted with an aqueous hydrolyzing solution comprising at least 35% wt. of at least one mineral acid. According to various embodiments, said at least one mineral acid is selected from sulfuric acid, phosphoric acid or a mixture thereof. According to another embodiment, mineral acid content in said hydrolyzing solution is at least 40% wt., at least 50% wt., at least 60% wt., at least 65% wt. or at least 70% wt. According to still another embodiment, mineral acid content in said hydrolyzing solution is less than 90% wt., less than 85% wt., less than 80% wt., less than 75% wt., or less than 70% wt.

According to an embodiment, the weight ratio of said mineral acid in said hydrolyzing solution to cellulose in said input material is greater than 0.3, greater than 0.5, greater than 0.7, greater than 0.8, greater than 0.9 or greater than 1.0. According to another embodiment, the weight ratio of said mineral acid in said hydrolyzing solution to cellulose in said input material is less than 20, less than 15, less than 10, or less than 5.

According to an embodiment, said contacting with an aqueous hydrolyzing solution is conducted, at least partially, at a temperature greater than 15° C., greater than 20° C., greater than 25° C., greater than 30° C., greater than 35° C., or greater than 40° C. According to an embodiment, said contacting with an aqueous hydrolyzing solution is conducted, at least partially, at a temperature lower than 80° C., lower than 70° C., lower than 60° C., lower than 55° C., lower than 50° C., or lower than 40° C. According to another embodiment, said contacting with an aqueous hydrolyzing solution is conducted, at least partially, at a temperature in the range between 10° C. and 80° C., between 20° C. and 70° C., or between 30° C. and 60° C.

Any form of contacting said input material with said aqueous hydrolyzing solution is suitable, e.g. mixing.

Said contacting with an aqueous hydrolyzing solution results in cellulose hydrolysis. As used herein, hydrolysis means reducing the molecular weight of cellulose. Said hydrolysis forms a hydrolyzate comprising a mixture of water-soluble carbohydrates and optionally a solid fraction. According to an embodiment, said input material comprises lignin and lignin forms at least a portion of said solid fraction. According to the method of the second aspect, at least 10%, at least 20%, at least 30%, at least 40% or at least 50% of the cellulose is hydrolyzed to form a mixture of water-soluble carbohydrates. As used herein, the degree of hydrolysis is the weight ratio between the total amount of water-soluble carbohydrates and the amount of cellulose in said input material. Said mixture comprises monosaccharides, disaccharides and/or oligosaccharides. As used herein, oligosaccharides are carbohydrates composed of at least 3 monosaccharides. According to an embodiment, said mixture comprises both hexoses and pentoses.

Input materials of the invention differ in characteristics such as cellulose content, composition of other components (e.g. content of hemicellulose and lignin), degree of cellulose crystallinity, moisture content and physical dimensions. These differences lead to differences in the result of said contacting with said aqueous hydrolyzing solution when conducted at identical conditions. These results of contacting include the extent of decrystallization, the degree of hydrolysis and the composition of the carbohydrate mixture.

Contacting parameters can be modified in order to affect the results of contacting. These parameters include acid selection and acid concentration in said hydrolyzing solution, acid to input material weight ratio, contacting temperature and contacting mode. According to an embodiment, those contacting parameters are adjusted to the characteristics of the input material in order to achieve a desired extent of decrystallizing of said cellulose in said input material. As used herein, decrystallizing means reducing the degree of crystallinity, as determined, e.g. by X-ray diffraction microscopy with polarized light, Raman spectroscopy. According to an embodiment, contacting parameters are selected so that the degree of crystallinity is reduced by at least 10%, at least 20%, at least 30%, at least 40%, or at least 50%.

According to an embodiment, those contacting parameters are adjusted to the characteristics of the input material in order to achieve a desired composition of the carbohydrates in said water-soluble carbohydrates mixture. According to an embodiment, monosaccharides form less than 85% wt., less than 75% wt., less than 65% wt., less than 55% wt., or less than 50% wt., of the carbohydrates in said hydrolyzate mixture of water-soluble carbohydrates. According to another embodiment, oligosaccharides form at least 10% wt., at least 20% wt., at least 25% wt., or at least 30% wt., of the carbohydrates in said hydrolyzate mixture of water-soluble carbohydrates.

The method of the second aspect comprises contacting said hydrolyzate with an extractant comprising a first solvent S1 and a second solvent S2, to form a residue and an acid-comprising extract. S1 is characterized by forming a single phase when mixed with an identical weight of 70% sulfuric acid aqueous solution at 25° C. According to an embodiment, S1 forms a single phase when mixed with 1.5 weights, 2 weights, 2.5 weights, 3.0 weights, 3.5 weight or 4.0 weights of 70% sulfuric acid aqueous solution at 25° C. According to an embodiment, said extractant comprises another organic solvent, (e.g. a water-immiscible ketone such as diethyl ketone), e.g. at least 1%, at least 3% or at least 5% of another solvent.

According to an embodiment, S1 is, or comprises, a solvent selected from the group consisting of alcohols comprising 3 to 6 carbon atoms and mixtures thereof. According to another embodiment, S1 is, or comprises, a solvent selected from the group consisting of tert-butyl alcohol, tert-amyl alcohol a mixture thereof. According to an embodiment, S1 is, or comprises, tert-amyl alcohol.

According to an embodiment, S1 comprises at least 65% wt., at least 70% wt., at least 75% wt., at least 80% wt., at least 85% wt., or at least 90% wt., of said extractant.

S2 has a solubility in water at 25° C. of less than 6% wt., less than 4% wt., less than 3% wt., less than 2% wt., or less than 1% wt. According to an embodiment, S2 is, or comprises, a solvent selected from the group consisting of saturated and unsaturated C5 to C12 hydrocarbons, dichloromethane, chloroform, halogen-substituted hydrocarbon and fluorine-substituted hydrocarbons. According to an embodiment, S2 is, or comprises, a solvent selected from a group consisting of decane and dodecane.

According to an embodiment, S2 comprises at least 1% wt., at least 2% wt., at least 3% wt., at least 4% wt., at least 5% wt., or at least 6% wt., of said extractant. According to an embodiment, S2 content of said extractant is modified during said contacting, e.g. by adding S2.

According to an embodiment, S2/S1 wt./wt. ratio in said extractant is less than 2, less than 1.5, less than 1, less than 0.8, less than 0.6, less than 0.4, or less than 0.2. According to another embodiment, S2/S1 wt./wt. ratio in said extractant is greater than 0.01, greater than 0.05, greater than 0.1, greater than 0.15, or greater than 0.2.

According to an embodiment, S2 is, or comprises, a hydrocarbon, S1 is, or comprises, tert-amyl alcohol and S2/S1 wt./wt. ratio in said extractant is less than 2, less than 1.5, less than 1, less than 0.8, less than 0.6, less than 0.4, or less than 0.2. According to another embodiment, S2 is, or comprises, a hydrocarbon, S1 is, or comprises, tert-amyl alcohol and S2/S1 wt./wt. ratio in said extractant is greater than 0.01, greater than 0.05, greater than 0.1, greater than 0.15, or greater than 0.2.

According to an embodiment, S2 is, or comprises, a hydrocarbon, S1 is, or comprises, tert-butyl alcohol and S2/S1 wt./wt. ratio in said extractant is less than 2, less than 1.5, less than 1, less than 0.8, less than 0.6, less than 0.4, or less than 0.2. According to another embodiment, S2 is, or comprises, a hydrocarbon, S1 is, or comprises, tert-butyl alcohol and S2/S1 wt./wt. ratio in said extractant is greater than 0.01, greater than 0.05, greater than 0.1, greater than 0.15, or greater than 0.2.

According to various embodiments, said contacting said hydrolyzate with an extractant is of multiple steps and is conducted in a counter-current or a cross-current mode. According to another embodiment, in said contacting, extractant to hydrolyzate flux wt./wt. ratio is in a range between 1:1 and 10:1, between 1.1:1 and 8:1, between 1.2:1 and 6:1 or between 1.3:1 and 4:1. According to an embodiment, said contacting is conducted at a temperature in the range between 1° C. and 60° C., between 5° C. and 55° C., or between 10° C. and 50° C.

Contacting said hydrolyzate with said extractant according to the method of said second aspect forms an acid-comprising extract, which preferably comprises at least 70% wt. of the acid and/or less than 10% wt. of the carbohydrates in said hydrolyzate. According to an embodiment, said extract of the second aspect comprises at least 75% wt., at least 80% wt., at least 84% wt., at least 88% wt., at least 90% wt., at least 92% wt., or at least 94% wt., of the acid in said hydrolyzate. According to an embodiment, said extract of the second aspect comprises less than 8% wt., less than 7% wt., less than 6% wt., less than 5% wt., less than 4% wt., or less than 3% wt., of the carbohydrates in said hydrolyzate. This embodiment therefore prioritizes sugar extraction over acid extraction.

According to an embodiment, acid/carbohydrate wt./wt. ratio in said extract is greater than acid/soluble carbohydrate wt./wt. ratio in said hydrolyzate by a factor of at least 2, at least 3, at least 4, at least 5, at least 6.

Contacting said hydrolyzate with said extractant according to the method of said second aspect forms a residue (e.g. a solid comprising precipitated carbohydrates), which typically comprises one or more of mineral acid, water-soluble carbohydrates (e.g. monosaccharides, disaccharides and/or oligosaccharides, preferably all three), optionally cellulose and optionally a solid fraction (e.g. comprising lignin). The extractant and/or solvents therein (e.g. S1 and/or S2) are preferably capable of precipitating carbohydrates. Since the majority of the acid in the hydrolyzate transfers to the extractant, the residue is depleted in acid. According to another embodiment, the mineral acid content of said first residue is less than 500 Kg, less than 400 Kg, less than 300 Kg, less than 200 Kg, or less than 100 Kg, per ton of said input material.

According to an embodiment, said residue is in fact an acid-depleted hydrolyzate. According to an embodiment, at least a fraction of said residue, is heated, whereby oligosaccharides hydrolyze, along with cellulose, if present, to form an aqueous solution comprising low molecular weight carbohydrate and mineral acid. According to another embodiment, said at least a fraction of said residue is combined with at least one other stream comprising oligosaccharides and/or cellulose for said heating. Said oligosaccharides hydrolysis is also referred to herein as second hydrolysis and the aqueous solution formed by said second hydrolysis is also referred to as second hydrolyzate.

According to the method of the second aspect, mineral acid is recovered from said extract and recovering comprises fractionating said modified extract into an S1-enriched fraction and an acid-enriched fraction. As used herein, S1-enriched fraction is a fraction having S1/acid wt./wt. ratio greater than that in the extract and acid-enriched fraction is a fraction having acid/S1 wt./wt. ratio greater than that in the extract. According to an embodiment, said S1-enriched fraction comprises less than 10% wt., less than 5% wt., less than 4% wt., less than 3% wt., less than 2% wt., or less than 1% wt. acid. According to an embodiment, said acid-enriched fraction comprises less than 10% wt., less than 5% wt., less than 4% wt., less than 3% wt., less than 2% wt., or less than 1% wt. S1.

According to an embodiment, said fractionating comprises contacting with S2. According to an embodiment, said acid-comprising extract is contacted with S2 to form two fractions, a light S1-enriched phase comprising S1 and S2 and a heavy aqueous acid-enriched phase. According to an embodiment, said contacting is conducted in a counter-current mode. Alternatively, or additionally, said fractionating said acid-comprising extract comprises evaporating S1.

The method of the second aspect comprises reusing said S1-enriched fraction to form said extractant. According to an embodiment, said reusing comprises at least one of drying, separation of a bleed for purification and addition of another solvent, e.g. S2. According to another embodiment, said reusing said S1-enriched fraction comprises separation of S1 from S2 by distillation.

The method of the second aspect further comprises reusing said acid-enriched fraction to form said aqueous hydrolyzing solution. According to an embodiment, acid/water wt./wt. ratio in said acid-enriched fraction is greater than 80%, greater than 85%, greater than 90%, greater than 95%, or greater than 100%, of that ratio in said hydrolyzing solution. According to an embodiment, said reusing comprises combining with a make-up acid to cover for the acid present in the residue.

The second aspect of the present invention provides a carbohydrate mixture produced according to said method, comprising at least 1 ppm, at least 5 ppm, at least 10 ppm, at least 15 ppm, or at least 20 ppm, of S1. According to a related embodiment, said S1 is, or comprises, a solvent selected from the group consisting of tert-butyl alcohol and tert-amyl alcohol.

As explained for the first aspect, the basic logic indicates that the potential gain in acid separation yield on using more hydrophilic extractants is outweighed by the costs related to reduced carbohydrate yields and generation of related degradation products. That has probably demotivated the use of more hydrophilic extractants, which seems to be the reason for selecting only extractants with an intermediate hydrophilicity.

The method of the first aspect solved these issues and enabled combining these seemingly conflicting goals of reaching high acid recovery yield and high carbohydrates production yield, by using as extractant a hydrophilic extractant and adding S2 to the extract, whereby carbohydrates separate into a second residue. The method of the second aspect provides another solution to this conflict. It involves contacting said hydrolyzate with an extractant comprising a relatively large fraction of the hydrophilic solvent S1 and a relatively small fraction of the hydrophobic S2. Results have shown that contacting said hydrolyzate with said extractant forms a residue and an acid-comprising extract, said extract comprises a large fraction of the mineral acid in said hydrolyzate, but only a minimal fraction of the water-soluble carbohydrates. Recovering the acid from said extract via said fractionating the extract forms an acid-enriched phase comprising the majority of the acid, but only a minimal content of water-soluble carbohydrates. In case reconcentration is required for reusing said acid, carbohydrates yield loss is minimal.

Hence, both the method of the first aspect and the method of the second aspect combine high yield of mineral acid separation from the hydrolyzate and high yields of carbohydrates production.

The inventors have found that, in some circumstances, recovery of S1 is lower than expected.

Example 5 shows investigations into this phenomenon. Condensing and analyzing the unknowns has indicated that the loss in S1 recovery was due to formation of alkenes by dehydration of S1, e.g. TAA, the results being confirmed by GC/MS. Without wishing to be bound by theory, the lower recovery of S1 is therefore thought to be due to formation of alkenes by dehydration of S1 solvents, especially alcohols, particularly tertiary alcohols such as tertiary amyl alcohol, with the alkenes then evaporating, hence the solvent loss. The inventors have found that the problem of solvent loss can be solved by (i) higher water activity in the system, (ii) lower temperature or acid concentration, (iii) including some phosphoric acid in the hydrolysis acid, e.g. using a $H_3PO_4$:$H_2SO_4$ (PA:SA) mix, (iv) exchanging TAA with the relatively more stable TBA (which forms isobutylene), or (v) by blending TBA (and/or TAA) with a ketone, e.g. a water immiscible ketone, such as diethylketone (DEK). These features, either alone or in any combination of two or more, form preferred aspects of the invention.

As noted above, a preferred aspect of the invention involves increasing the amount of water used in the system. A typical acid solution used for hydrolysis is 70% acid (and therefore 30% water). The weight ratio of acid to water is thus 2.33 (70/30). This ratio will be slightly less in the extract after acid extraction, typically around 2.2. Increasing the proportion of water in the hydrolyzing solution has been found to increase recovery of S1.

Thus, a preferred aspect of the present invention is the use of an aqueous hydrolyzing solution with an acid/water weight ratio of less than 2.2, e.g. 0.50 to 1.85, preferably 0.7 to 1.5, especially around 1 (i.e. a hydrolyzing solution of 50 wt % acid, 50 wt % water) in the processes of the invention.

The higher water content has the additional advantage of offering a better S1 extraction from the acid due to increased polarity in the polar phase.

Additionally, or alternatively, water can be added after the removal of the sugar lignin residue, e.g. in the desolventizer. This will influence sugar rejection, probably by increasing the volume of the phase containing the rejected sugar, which will probably lead to a slightly higher acid amount in this phase. It will also help S1 removal as explained above. These advantages should be balanced against the increased cost of water removal.

Another preferred aspect is the use of a lower temperature and/or a lower acid concentration. The inventors have found temperature and acid concentration to be the two main parameters that influence alkene formation. The acid concentration can be adjusted as described above, by increasing the proportion of water in the hydrolyzing solution. In order to use a lower temperature to reduce alkene formation, the step of contacting the hydrolyzate with an extractant and/or the step of modifying and/or the step of fractionating (preferably all) should preferably be performed at a temperature of 25° C. or less, particularly 15° C. or less, especially preferably 10° C. or less.

Where a distillation step is involved, this will typically require cooling of the streams after distillation to avoid the return of a warm stream of S1/S2 to distillation after extraction.

In all aspects of the invention it is preferred that the removal of S1 from the acid (e.g. by extraction using S2) is as complete as possible. Otherwise, remaining S1 can be lost in the concentrated acid especially if there is a need for concentrating the acid further by evaporation of water or solvents.

A further preferred aspect is the inclusion of phosphoric acid into the hydrolyzing solution to reduce alkene yield. Thus, in a preferred aspect the process of the invention involves the use of a hydrolyzing solution in which the total amount of mineral acid comprises up to 50 wt % phosphoric acid, (i.e. up to 50 wt % of the mineral acid in the hydrolyzing solution is phosphoric acid), preferably up to 25 wt % (e.g. 5 to 25 wt %), especially preferably up to 10 wt % phosphoric acid, expressed as the proportion of phosphoric acid in comparison to mineral acid as a whole.

A further preferred aspect is the inclusion of tertiary butyl alcohol (TBA) in the extractant. Thus, a preferred aspect of the invention is the use of an extractant which comprises TBA, i.e. up to 100 wt % TBA, preferably up to 50 wt %, especially up to 25 wt. %, especially in combination with TAA. TBA generates isobutylene on dehydration which boils at −8° C. compared to TAA which generates 2-methyl-2 butene and 2-methyl-1butene which boil at 39° C. and 31° C. respectively. The low boiling point of isobutylene is believed to stop polymerization by effectively removing it from the acid by evaporation. TBA is more stable than TAA, in contrast to TAA it is water soluble and thus coextracts more sugar during acid extraction. This aspect is therefore most preferred for embodiments of the invention comprising use of S2 in the extractant.

A further preferred aspect of all embodiments herein described is the inclusion of a water immiscible ketone (e.g. an aliphatic ketone, preferably an aliphatic ketone containing 5 to 7, especially 5, carbon atoms) preferably diethyl ketone in the extractant. Preferably the ketone is diethyl ketone (DEK), methyl propyl ketone (MPK), methyl isopropyl ketone (MIPK), cyclohexanone or mesityl oxide, especially preferably it is DEK, MPK or MIPK, particularly preferably diethyl ketone. Preferably, the extractant comprises 50-70 wt % water immiscible ketone.

This aspect is particularly preferred for embodiments of the invention comprising use of S2 in the extractant. The inventors have found an unexpected drop in TAA reactivity when mixing with water immiscible ketones such as DEK. DEK has been found to be superior to TBA and TAA when it comes to sugar co-extraction and pentane extraction, but the alcohols have much better acid extraction.

Other factors that will help to reduce the cost related to alcohol dehydration to alkenes and thus form preferred aspects of the invention include: (a) Using a closed system. The dehydration of alcohol is a reversible reaction, when allowing for the escape of products the yield will increase; and (b) Minimizing contact time between acid and alcohols at certain stages. The design of the process (vessel size and holding times) should aim for as small amount alcohols as possible to be present when reaction rates are high.

The above means of solving the problem of alkene formation thus constitute preferred aspects of the invention, either individually or in any combination.

The inventors have surprisingly found that the conversion of alcohols to alkenes can be used as a means for recovering S1 from S1/S2 mixtures. In the event that alkenes form during the processes of the invention, S2 can then be separated from the alkenes by distillation. For example, octanol (S2) can be separated from alkenes formed by TBA (S1) by distillation. After separation from S2, the alkenes can be rehydrated to the relevant alcohol using conventional methods, e.g. by mixing isobutylene (from TBA) or 2-methyl-2 butene and 2-methyl-1butene (from TAA) with steam over an acid catalyst (e.g. phosphoric acid substituted ionic exchange matrix), the corresponding alcohols will be formed and can then be reused in the processes of the invention. Thus, a further aspect of the invention involves the conversion of S1 to alkenes, separation of said alkenes from S2 by distillation and rehydration of the alkenes to recover S1. Similarly, conversion of alcohol solvent to alkenes can be used to separate S1 from the hydrolysis acid, i.e. by stripping the alkenes from the reaction (i.e. heating S1 and acid to form alkenes, removing the alkenes by evaporation assisted by gas stripping and/or vacuum to stop acid catalyzed polymerization of alkenes) and reforming them to the alcohol for reuse.

A further aspect of the invention involves the rehydration of alkenes to form S1 for use in the extractant. Ethanol fermentation of sugars (e.g. lignocellulose derived sugars) produces some fusel oil which can be separated from ethanol at distillation. Fusel may be transformed into TAA via the precursors 2-methyl-2 butene and 2-methyl-1butene. Additionally, or alternatively, 2-methyl-2 butene and 2-methyl-1butene, produced from dehydration of TAA during the process of the invention may be included in this reaction to form TAA. In this way, S1 may be produced for use in the extraction step of the invention (or for use elsewhere) either from fusel or alkenes.

Unless otherwise specified, the term "sugar" as used herein should generally be understood to be interchangeable with "carbohydrate" and thus encompasses structural carbohydrates, polysaccharides, monomeric sugars, oligomeric or crystalline regions of cellulose, nanocellulose crystal whiskers, and glucans. Soluble carbohydrates include monosaccharides, disaccharides and/or oligosaccharides.

The methods of the present invention as herein described are suitable for processing cellulose-containing material and/or for producing carbohydrates, e.g. water-soluble carbohydrates, particularly, monosaccharides, disaccharides and/or oligosaccharides. The methods can also be viewed as methods for separating mineral acids from the hydrolysate of the invention. The invention can also be viewed as the use of solvent S1 as herein described, in the recovery of a mineral acid from a cellulose hydrolysis process or cellulose hydrolysate. The methods as herein described can also be extended to the production of down-stream products such as alcohols. Thus in a preferred aspect, fermenting the sugars and distilling alcohol from the resulting fermented mixture allows the process to be extended to produce alcohol. The methods as herein described therefore optionally further comprise one or more of the following steps:

(v) subjecting the residue comprising sugars to an oligosaccharide cleavage reaction to yield fermentable carbohydrates (e.g. an aqueous solution of fermentable carbohydrates);

(vi) fermenting said fermentable carbohydrates (e.g. sugars) and distilling alcohol (e.g. ethanol or butanol) from the resulting fermented mixture.

The overall production process (e.g. of alcohol or other end products) may, if desired, be performed at a set of production sites, e.g. with production of the fermentable sugars on one site and fermentation and distillation at another. Equally, the acid hydrolysis, acid removal and extraction solvent removal may be performed at one site with the oligosaccharide cleavage and other downstream steps being performed at another site.

Where the next step of the process is carried out at another site, the sugars will typically be transported as an aqueous solution. By subjecting the residue to an oligosaccharide cleavage reaction, fermentable sugars can be produced. Fermenting said fermentable sugars and distilling alcohol from the resulting fermented mixture allows the process to be extended to produce alcohol.

The oligosaccharide cleavage reaction may be effected enzymatically or alternatively, and preferably, by acid hydrolysis. The residue of acid retained in the unwashed first residue may be adequate for oligosaccharide cleavage to proceed via such a second acid hydrolysis step. Alternatively further acid may be added, for example to bring the acid content of the sugar solution up to about 0.1 to 5 wt %, especially, 0.2 to 4 wt %, preferably 0.5 to 2 wt %, particularly about 4 wt % or about 1 wt %. Addition of excess acid is undesirable as, following a second acid hydrolysis, the resulting hydrolysate must be adjusted to a pH suitable for the microorganisms responsible for fermentation (generally yeasts). This second hydrolysis may be effected under conventional conditions for weak acid hydrolysis of oligosaccharides, e.g. a temperature of 100 to 180° C., particularly about 120° C., a pressure of 1 to 10 bar, preferably 2 bar, and a duration of about 0.5 to 4 hours, particularly about 1 to 3 hours, preferably around 2 hours.

Before fermentation, the fermentable sugars in aqueous solution are preferably filtered to recover any lignin. This is preferably washed to recover any entrained sugars for fermentation and compressed for use as a fuel, e.g. to provide energy for one or more of the steps in the overall alcohol production process.

The microorganism used in the fermentation step may be any microorganism capable of converting fermentable sugars to alcohol, e.g. brewer's yeast. Preferably however a yeast or yeast mixture is used which can transform the pentoses yielded by hemicellulose hydrolysis as well as the hexoses yielded by cellulose hydrolysis. Such yeasts are available commercially. The use of microorganisms that can transform pentoses to alcohol (e.g. *Pichia stipitis*, particularly *P. stipitis* CBS6054), particularly in combination with ones which can transform hexoses to alcohol, is especially preferred. Where fermentation is performed using microorganisms other than brewer's yeast (e.g. *C. beijerinckii* BA101), alcohols other than ethanol, in particular butanol, can be produced and these too can be used as biofuels. The invention covers the production of such other alcohols.

Distillation of alcohol from the fermented sugars may be effected in conventional fashion. The sugars produced using the invention can be fermented or respired by Baker's yeast or other microorganisms to yield many different biologically produced compounds such as glycerol, acetone, organic acids (e.g. butyric acid, lactic acid, acetic acid), hydrogen, methane, biopolymers, single cell protein (SCP), antibiotics and other pharmaceuticals. Specific proteins, enzymes or other compounds could also be extracted from cells grown on the sugars. The sugars moreover may be transformed into desired end products by chemical and physical rather than biological means, e.g. reflux boiling of xylose will yield furfural. The invention thus also covers the production of all such other produced compounds besides alcohols. Thus, processing of the sugar/carbohydrate compositions or aqueous solutions of sugars/carbohydrates produced by the processes described herein to form the above products thus forms a further aspect of the invention. The compositions produced by the processes of the invention also form a further aspect.

Viewed from another aspect, the invention provides apparatus for use in the processes herein described, said apparatus comprising:
 a first hydrolysis reactor;
 an acid reservoir arranged to supply the aqueous hydrolysing solution as herein described to said first hydrolysis reactor;
 a first separator arranged to receive hydrolysate from said first hydrolysis reactor and to discharge carbohydrate (e.g. sugar) slurry;
 an extraction solvent reservoir arranged to supply an extraction solvent, i.e. the extractant as herein described, to said first separator;
 a second separator arranged to receive an acid-comprising extract from said first separator and to discharge extraction solvent S1 and aqueous acid;
 optionally an acid re-concentration unit arranged to receive aqueous acid from said second separator; and
 optionally, recycling conduits arranged to return extraction solvent (S1) to said first separator or an extraction solvent reservoir and/or to return concentrated aqueous acid to said reactor or an acid reservoir.

It is preferred that the apparatus also comprises a recycling conduit to return concentrated aqueous acid to said first hydrolysis reactor or an acid reservoir.

In a preferred aspect, the apparatus further comprises an organic solvent reservoir arranged to supply an organic solvent (e.g. S2 as herein described) to said second separator; and optionally a rectifier arranged to receive an extraction solvent/organic solvent mixture from said second separator and to discharge an extraction solvent and, separately, an organic solvent.

The apparatus preferably also comprises components for feeding cellulosic material to the reactor. Conveniently, it also comprises components for the downstream handling of the carbohydrate slurry, e.g. further hydrolysis reactors, reservoirs for a base for neutralizing the residual acid, fermentors and distillation units. To allow for continuous operation of the process when individual steps are performed batch-wise, individual units within the apparatus may be duplicated, i.e. with such units being in parallel, so that one may be in operation while the other is being loaded/unloaded. This is particularly the case for the second acid hydrolysis, the fermentation, the distillation, and the lignin separation steps.

Preferably, a desolventising unit which is capable of acting as a second hydrolysis reactor and thus comprises heating and pressurising means and is arranged to discharge a mixture containing fermentable sugars is also present.

The invention will now be further described with reference to the following non-limiting examples:

EXAMPLES

Example 1

Modifying an Acid-Comprising Extract by Means of Adding S2

Example 1 tested the use of tert-amyl alcohol (TAA) and n-pentane as S1 and S2, respectively, and glucose as the carbohydrate.

A synthetic acid-comprising extract solution was prepared, containing 4.5% wt. glucose, 24.4% wt. sulfuric acid, 10.5% wt. water and 60.6% wt TAA (S1/mineral acid wt./wt. ratio of about 2.5). This synthetic extract demonstrates an extract formed on contacting hydrolyzate with an extractant composed of TAA as S1. For simplicity, only glucose is used as co-extracted carbohydrate.

24.2 g of the acid-comprising extract was mixed with 6.3 g n-pentane at room temperature (S2/S1 wt./wt. ratio of 0.43). The mixture was then allowed to settle overnight. A heavy, second residue, phase was observed. It was separated, weighed (about 1 gr) and analyzed. This second residue contained 26.6% wt. of the glucose present originally in the extract and 9.8% wt. of the sulfuric acid there.

These results demonstrate that, on mixing S2 with acid-comprising extract, carbohydrates are preferentially rejected into the second residue.

Examples 2-4

Modifying an Acid-Comprising Extract by Means of Adding S2

Examples 2-4 tested the use of TAA and n-pentane as S1 and S2, respectively, and maltose as the carbohydrate.

A simulated hydrolyzate was prepared, composed on 61.8% wt. sulfuric acid, 26.7% wt. water and 11.5% wt.

maltose. Three synthetic acid-comprising extract solutions were prepared by adding TAA to said simulated hydrolyzate. Their compositions are summarized in Table 1. Those extracts were modified by mixing with n-pentane at room temperature. After settling, a heavy second residue phase and a light modified extract phase were observed in all three. The phases were separated, weighed and analyzed. Total S2/S1 ratios and relative weights of the phases are summarized in table 1. The results of the analysis and related calculations are presented in Tables 2 and 3.

TABLE 1

Compositions of simulated extracts, S2/S1 ratios and phase weight ratios

| Example # | Synthetic extract composition (% wt.) | | | | S1/acid wt./wt. | S2/S1 wt./wt. in total mixture | Light phase/ heavy phase wt./wt. ratio |
|---|---|---|---|---|---|---|---|
| | TAA | Acid | Water | Maltose | | | |
| 2 | 59.8 | 24.8 | 10.8 | 4.6 | 2.4 | 0.65 | 17.0 |
| 3 | 63.3 | 22.7 | 9.8 | 4.2 | 2.8 | 0.71 | 15.8 |
| 4 | 68.9 | 19.2 | 8.3 | 3.6 | 3.6 | 1.29 | 34.4 |

TABLE 2

Analysis of the formed phases

| Example # | Light phase composition (% wt.) | | | Heavy phase composition (% wt.) | | |
|---|---|---|---|---|---|---|
| | $H_2SO_4$ | maltose | glucose | $H_2SO_4$ | maltose | Glucose |
| 2 | 20.0 | 0.43 | 0.35 | 26.7 | 27.1 | 9.2 |
| 3 | 17.8 | 0.24 | 0.21 | 24.9 | 33.2 | 12.2 |
| 4 | 12.9 | 0.20 | 0.23 | 24.1 | 28.7 | 13.2 |

TABLE 3

Carbohydrates rejection and distribution coefficients

| Example # | Carbohydrates in heavy phase out of total (% wt.) | Acid in heavy phase out of total (% wt.) | Water in heavy phase out of total (% wt.) | D[1] $H_2SO_4$ | D[1] maltose | D[1] glucose |
|---|---|---|---|---|---|---|
| 2 | 73 | 7.3 | 19.0 | 0.75 | 0.016 | 0.038 |
| 3 | 83 | 8.2 | 18.2 | 0.72 | 0.0073 | 0.017 |
| 4 | 74 | 5.1 | 11.6 | 0.53 | 0.0069 | 0.017 |

[1] D is the distribution coefficient, calculated as concentration in the light phase divided by that in the heavy phase.

These results demonstrate the following: (i) Modifying the acid-comprising extracts, by mixing with S2, results in the formation of a relatively small heavy second residue phase and a large light modified extract phase. (ii) The small heavy phase contained 73-83% of the carbohydrates originally present in the extract, but only 5-9% of the sulfuric acid originally present there. Displacement of the carbohydrates preferentially to sulfuric acid is also demonstrated by the distribution coefficients. (iii) A fraction of the water in the acid-comprising extract transfer to the second residue. The fraction of water transferred to the second residue is more than 2 times greater than the fraction of the acid transferred there, which means that the acid/water ratio in the modified extract (the light phase) is greater than that of the extract. (iv) The simulated hydrolyzate contained maltose as the sole carbohydrate. The analysis of the two phases, formed during extract modification, contain both maltose and glucose, indicating some hydrolysis of the maltose. Distribution coefficients of maltose are about twice smaller than those of glucose, confirming that higher molecular weight carbohydrates are more efficiently displaced from the extract. This result demonstrates the importance of the embodiment of adjusting decrystallization conditions to minimize formation of monosaccharides.

In summary: The results confirm that modifying the extracts rejects from the extract the majority of the co-extracted carbohydrate along with a significant amount of the water, while keeping the majority of the extracted acid in the modified extract. That means that (i) S1 with desired high common miscibility with sulfuric acid solution can be used in order to achieve high yield of mineral acid separation from the hydrolyzate; (ii) the co-extracted carbohydrates can be displaced from the extract by the modification before recovering the acid from the modified extract; (iii) that the recovered modified extract is low in carbohydrates, so that carbohydrate losses in case of acid reconcentration are minimal and (iv) reconcentration may not be required due to displacing water from the extract into said second residue.

Example 5

It was observed that, when adding pentane to a simulated extract feed of TAA:water and sulphuric acid (typical 64:11:25 wt %) a two phase system developed. after separating the phases a new organic phase appeared in the polar phase upon standing. If one shook the new two phase system vigorously, the phases rapidly separated to the same levels as prior to shaking, indicating that the appearance of an organic phase over the previously separated polar bottom phase was not due to slow phase separation. Furthermore, during two experiments extracting sulphuric acid from a spruce hydrolysate using TAA, and following the process to sugar and lignin with all recycling steps (using pentane as S2) substantial amounts (>50%) of the TAA were lost in the process. It was believed that these phenomena were due to dehydration of the alcohol form alkene by-products.

The above mentioned dehydration products were identified from mixtures of sulphuric acid and TAA by GC/MS and a method for their quantification by GC-FID has been developed.

The organic phase that appears from the polar phase after TAA extraction from acid by pentane, was confirmed to consist of least partially of TAA and at least partially alkenes. No such organic phase appeared when phosphoric acid (PA) was used instead of sulphuric acid in otherwise identical experiments.

Experiments were performed to investigate alkene production rates by mixing aqueous acid solution (typically 70 wt %) with TAA. The reaction was carried out in a rotavapor at atmospheric pressure at different temperatures. Alkene yield was calculated as mass loss. Reactions were 2 h except for the 25° C. experiments which were left for typically 16 hours. The results are shown in Tables 4 to 8 below.

The experimental conditions changed during the experiments, due to evaporation of solvents and products, especially at 50 and 80° C. 25 wt % acid concentration at the start of the experiment changed to 50 wt % at high temperatures. There were some alkanes left in the reaction pot, not distilled off, this leads to an underrepresentation of yield. The analyses done suggest that the amount of alkenes in the stillage is 5 wt % at 25° C. and 1-3% at 50° C. There was some alcohol in the condensed distillate, the TAA concentration in the distillate is 5-6 wt % at 80° C. and 1-2% at 50° C. All experiments are performed as open systems, thus showing a worst case scenario as products are continuously removed.

The results support the theory that acid catalyzed dehydration of TAA to 2-methyl-1 butene, 2-methyl-2 butene, and the three dimers of these.

TABLE 4

| Temperature ° C. | Acid wt % ($H_2SO_4$ + $H_3PO_4$) | Proportion $H_3PO_4$ in acid | Water wt % | Si | Yield (distillate g/100 g alcohol * h) |
|---|---|---|---|---|---|
| 25 | 25 | 0 | 11 | TAA | 2.0 |
| 25 | 25 | 0.25 | 11 | TAA | 0.2 |
| 25 | 25 | 0 | 11 | TAA | 1.1 |
| 25 | 25 | 0 | 15 | TAA | 0.0 |
| 50 | 25 | 0 | 11 | TAA | 34.0 |
| 50 | 25 | 0.25 | 11 | TAA | 10.0 |
| 50 | 50 | 0.6 | 22 | TAA | 18.0 |
| 50 | 25 | 0.6 | 11 | TAA | 4.0 |
| 50 | 25 | 1 | 11 | TAA | 0.0 |
| 50 | 50 | 0.25 | 22 | TAA | 6.0 |
| 50 | 25 | 0 | 11 | TBA | 2.1 |
| 50 | 25 | 0 | 15 | TBA | 1.3 |
| 50 | 25 | 0 | 11 | TAA:DEK (1:1) | 6.9 |
| 80 | 50 | 0.6 | 22 | TAA | 39.0 |
| 80 | 25 | 0.6 | 11 | TAA | 41.0 |
| 80 | 25 | 1 | 11 | TAA | 27.0 |
| 80 | 50 | 1 | 22 | TAA | 41.0 |
| 80 | 50 | 0.25 | 22 | TAA | 28.0 |
| 80 | 25 | 0 | 11 | TAA:DEK (1:2) | 44.0 |

TABLE 5

Influence of solvent system

| Temperature ° C. | Acid wt % ($H_2SO_4$ + $H_3PO_4$) | Proportion $H_3PO_4$ in acid | Water wt % | Si | Yield (distillate g/100 g alcohol * h) |
|---|---|---|---|---|---|
| 50 | 25 | 0 | 15 | TBA | 1.27 |
| 50 | 25 | 0 | 11 | TBA | 2.05 |
| 50 | 25 | 0 | 11 | TAA:DEK 1:1 | 6.94 |
| 50 | 25 | 0 | 11 | TAA | 34 |
| 50 | 50 | 0.25 | 22 | TAA | 5.8 |
| 50 | 25 | 0.25 | 11 | TAA | 10 |

TABLE 5-continued

Influence of solvent system

| Temperature ° C. | Acid wt % ($H_2SO_4$ + $H_3PO_4$) | Proportion $H_3PO_4$ in acid | Water wt % | Si | Yield (distillate g/100 g alcohol * h) |
|---|---|---|---|---|---|
| 50 | 25 | 0.6 | 11 | TAA | 4 |
| 50 | 50 | 0.6 | 22 | TAA | 18 |
| 50 | 25 | 1 | 11 | TAA | 0 |

TABLE 6

Influence of PA

| Temperature ° C. | Acid wt % ($H_2SO_4$ + $H_3PO_4$) | Proportion $H_3PO_4$ in acid | Water wt % | Si | Yield (distillate g/100 g alcohol * h) |
|---|---|---|---|---|---|
| 50 | 25 | 0 | 11 | TAA | 34 |
| 50 | 25 | 0.25 | 11 | TAA | 10 |
| 50 | 25 | 0.6 | 11 | TAA | 4 |
| 50 | 25 | 1 | 11 | TAA | 0 |

TABLE 7

Influence of temperature

| Temperature ° C. | Acid wt % ($H_2SO_4$ + $H_3PO_4$) | Proportion $H_3PO_4$ in acid | Water wt % | Si | Yield (distillate g/100 g alcohol * h) |
|---|---|---|---|---|---|
| 25 | 25 | 0 | 11 | TAA | 2.0 |
| 25 | 25 | 0 | 11 | TAA | 0.4 |
| 50 | 25 | 0 | 11 | TAA | 34.0 |
| 50 | 25 | 0 | 11 | TAA:DEK 1:1 | 6.4 |
| 80 | 25 | 0 | 11 | TAA:DEK 1:1 | 44.0 |

TABLE 8

Influence of water

| Temperature ° C. | Acid wt % ($H_2SO_4$ + $H_3PO_4$) | Proportion $H_3PO_4$ in acid | Water wt % | Si | Yield (distillate g/100 g alcohol * h) |
|---|---|---|---|---|---|
| 25 | 25 | 0 | 11 | TAA | 0.4 |
| 50 | 25 | 0 | 11 | TBA | 2.1 |
| 25 | 25 | 0 | 15 | TAA | 0.0 |
| 50 | 25 | 0 | 15 | TBA | 1.3 |

Table 8 shows that using 63% acid for hydrolysation (wt. ratio acid/water=1.7, rather than the typical 2.3—this seemingly small change changes the moles of water:acid from 2.3 to 3.2)

As seen in Experiment 5, an increase of water activity to an acid/water ratio of 1.7 reduces alkene yield from TAA at 25° C. from 1.3 g to 0 g, and with TBA at 50° C. from 2.2 g to 1.1 g.

The results suggest that:
Mixtures of TBA and DEK or TAA and DEK for S1 are preferred.
Inclusion of phosphoric acid in the acid mixture in the range 0.05 to 0.25 parts to total acid is preferred.
Water could be added after acid extraction, this lowers reactivity, and may improve alcohol extractability.

Example 6

Influence of DEK 45.1 g of spruce wood chips, with 11 wt % moisture, was added 119.2 g of a 69.8 wt % aqueous sulfuric acid solution. The mixture was stirred for 45 minutes at 45° C. After this decrystallization step, approximately 30 g of hydrolysate was transferred to four centrifugation bottles. The hydrolysate was added 1.5 part of S1 solution, four different S1 solutions were used, DEK:TBA (5:5), DEK:TBA(6:4), DEK:TBA (7:3) and DEK:TBA (8:2). After addition the solution was vigorously shaken and centrifuged. The supernatant was removed and the residue was again extracted with S1 of same amount and composition as the first time, this was repeated for a total of 4 extractions. The carbohydrate/lignin residue was analyzed for residual acid content. Pure TBA typically gives an acid consumption (not extracted) of 70 kg sulphuric acid/ton feed, while DEK gives 250 kg. As can be seen from the table below, 50-30% TBA in DEK most preferably 30% gives good acid extraction and will give lower alkene production and better extraction by S2.

| Si | Acid consumption (kg/ton dry feed) |
|---|---|
| DEK:TBA (5:5) | 80.6 |
| DEK:TBA (6:4) | 81.6 |
| DEK:TBA (7:3) | 90.3 |
| DEK:TBA (8:2) | 118.6 |

FIGS. 1 and 2 show results obtained for pentane extraction of a synthetic feed stream (25% sulphuric acid, 15% water, remainder TBA and DEK) extracted by 1 part pentane per 1 part feed.

The invention claimed is:
1. A method comprising
   (i) contacting a cellulose-comprising input material with an aqueous hydrolyzing solution comprising at least 35% wt. of at least one mineral acid to form a hydrolyzate comprising a mixture of water-soluble carbohydrates and optionally a solid fraction;
   (ii) contacting said hydrolyzate with an extractant comprising a first solvent S1, to form (a) a solid first residue comprising precipitated carbohydrates and (b) an acid-comprising extract;
   (iii) separating said acid-comprising extract from said solid first residue;
   (iv) modifying said acid-comprising extract to form (a) a liquid second residue comprising dissolved carbohydrates and (b) an acid-comprising modified extract, wherein said modifying said acid-comprising extract comprises combining said extract with a second solvent S2;
   (v) fractionating said modified extract into an S1-enriched fraction and an acid-enriched fraction;
   (vi) reusing said S1-enriched fraction to form said extractant; and
   (vii) reusing said acid-enriched fraction to form said aqueous hydrolyzing solution; wherein
   (a) at least 10% wt. of the cellulose is hydrolyzed and said mixture of water-soluble carbohydrates comprises monosaccharides, disaccharides and/or oligosaccharides;
   (b) S1 forms a single phase when mixed with an identical weight of 70% sulfuric acid aqueous solution at 25° C.;
   (c) S1 is at least 65% wt. of said extractant; and
   (d) said acid-comprising extract comprises at least 60% wt. of the acid and at least 5% wt. of the carbohydrates in said hydrolyzate.

2. A method according to claim 1, wherein the weight ratio of said mineral acid in said aqueous hydrolyzing solution to cellulose in said input material is greater than 0.5.

3. A method according to claim 1, wherein the weight ratio of said mineral acid in said aqueous hydrolyzing solution to cellulose in said input material is less than 20.

4. A method according to claim 1, wherein said aqueous hydrolyzing solution comprises a mixture of sulfuric acid and phosphoric acid.

5. A method according to claim 1, wherein said contacting with an aqueous hydrolyzing solution is conducted, at least partially, at a temperature in a range between 15° C. and 80° C.

6. A method according to claim 1, wherein monosaccharides form less than 85% wt. of the water-soluble carbohydrates in said hydrolyzate.

7. A method according to claim 1, wherein said S1 is selected from the group consisting of alcohols comprising 3 to 6 carbon atoms and mixtures thereof.

8. A method according to claim 1, wherein said S1 is selected from the group consisting of tert-butyl alcohol, tert-amyl alcohol and mixtures thereof.

9. A method according to claim 1, wherein acid content of said solid first residue is less than 500 Kg per ton of said input material.

10. A method according to claim 1, wherein said acid-comprising extract comprises less than 80% wt. of the carbohydrates in said hydrolyzate.

11. A method according to claim 1, wherein said S2 has solubility in water of less than 6% at 25° C.

12. A method according to claim 1, wherein S2 is selected from the group consisting of saturated and unsaturated C5 to C12 hydrocarbons, dichloromethane, chloroform, halogen-substituted hydrocarbon and fluorine-substituted hydrocarbons.

13. A method according to claim 1, wherein said extractant comprises S2.

14. A method according to claim 1, wherein S2/S1 wt./wt. ratio in said modified extract is less than 2.

15. A method according to claim 1, wherein S2/S1 wt./wt. ratio in said modified extract is greater than 0.01.

16. A method according to claim 1, wherein S2 is a hydrocarbon, S2 is tert-amyl alcohol and S2/S1 wt./wt. ratio in said modified extract is greater than 0.01.

17. A method according to claim 1, wherein S2 is a hydrocarbon, S1 is tert-amyl alcohol and S2/S1 wt./wt. ratio in said modified extract is less than 2.

18. A method according to claim 1, wherein said modifying said acid-comprising extract comprises changing the temperature of said extract.

19. A method according to claim 18, wherein said changing the temperature comprises lowering the temperature of said acid-comprising extract by at least 10° C.

* * * * *